United States Patent [19]
Gurusiddaiah et al.

[11] Patent Number: 4,759,928
[45] Date of Patent: Jul. 26, 1988

[54] ANTIBIOTIC: TREPONEMYCIN

[75] Inventors: Sarangamat Gurusiddaiah, Pullman, Wash.; Shrikrishna Singh, Pittsburgh, Pa.

[73] Assignee: Washington State University Research Foundation, Pullman, Wash.

[21] Appl. No.: 824,733

[22] Filed: Jan. 31, 1986

[51] Int. Cl.$^4$ .......................... A61K 35/74; C12P 1/06
[52] U.S. Cl. ..................................... 424/122; 435/169
[58] Field of Search .......................... 424/122; 435/169

[56] References Cited

U.S. PATENT DOCUMENTS 2,999,048  9/1961  Donovick et al. .................. 424/122

OTHER PUBLICATIONS

Chemical Abstracts 103: 50922t (1985).
S. K. Singh, S. Gurusiddaiah, and J. W. Whalen, 1985, Treponemycin, A Nitrile Antibiotic Active Against *Treponema hyodysenteriae*, Antimicrobial Agents and Chemotherapy, 27, 239–245.
L. Anderton and R. W. Rickards, 1965, Some Structural Features of Borrelidin, An Antiviral Antibiotic, Nature: 206: p. 269.
T. Korzybski, Z. Kowszyk-Ginder, and W. Kurytowicz, 1978, Antibiotics, vol. II, pp. 1198–1199, ASM Publications.
R. M. Silverstein and G. C. Bassler, 1968, Spectrometric Identification of Organic Compounds, p. 256, John Wiley and Sons; New York.

*Primary Examiner*—Jerome D. Goldberg
*Attorney, Agent, or Firm*—Wells, St. John & Roberts

[57] ABSTRACT

Two strains of Streptomyces were identified as *Streptomyces albovinaceous*. Both isolates produced an antibiotic when grown in liquid culture medium containing homogenized oats. The antibiotic (Treponemycin) was isolated from the culture broth by solvent extraction and purified. The antibiotic showed inhibitory activity against several species of bacteria, especially *Treponema hyodysenteriae*, the causative agent of swine dysentery. In view of the oral 50% lethal dose of 400 mg/kg and its low MIC against four strains of *T. hyodysenteriae*, the antibiotic has value as a swine dysentery therapeutic. The antibiotic lends itself readily to production of a tetrahydro derivative, a primary amine, a dimethyl ester and a hydrochloride esters and salts of these compounds, and hydrates of these compounds and of the esters or salts can also be produced for pharmaceutical usages.

14 Claims, 7 Drawing Sheets fig 1 fig 2

ANTIBIOTIC: TREPONEMYCIN

FIELD OF THE INVENTION

This disclosure relates to a new antibiotic: Treponemycin, new strains of Streptomyces albovinaceous, from which the antibiotic is produced, and treatment and prophylactic methods and compositions for combatting infectious diseases such as dysentery in swine caused by *Treponema hyodysenteriae*.

BACKGROUND OF THE INVENTION

In the course of a screening program to find new and active compounds from soil microorganisms, we isolated two cultures of Streptomyces sp. (isolates 124 and 275). Both of these cultures produce an active antibiotic substance which showed a strong inhibitory activity in vitro against four pathogenic strains of *Treponema hyodysenteriae*, the causative agent of swine dysentery. It also showed useful activity against other microorganisms that cause infectious diseases in both humans and animals. This disclosure describes the characteristics of the antibiotic-producing organism and the isolation, purification, and characterization of the antibiotic produced by it.

Both soil isolates of Streptomyces sp. that produce Treponemycin were identified as *S. albovinaceous*. It has been reported that the same species of Streptomyces also produces another antibiotic (Nancimycin), which is active against gram-positive bacteria and certain viruses (R. Sonvick, J. F. Pagano, B. Brook, and J. Vandeputte, U.S. Pat. No. 2,999,048, 1961). The chemical and other properties of Nancimycin seem to be distinct from those of Treponemycin. For example, the three UV absorption bands of Nancimycin (at 225, 305, and 425 nm) are absent in the UV spectra of Treponemycin. Unlike Treponemycin, the antibiotic Nancimycin is a non-nitrogenous compound with a molecular formula of $C_{23}H_{30}O_{10}$ (Treponemycin, $C_{28}H_{43}O_6N$). In addition to these differences, the characteristic IR absorption band at 2,210 nm for the nitrile function of Treponemycin is absent in the IR spectra of Nancimycin. These characteristics demonstrate that Nancimycin and Treponemycin, although produced by the same species of Streptomyces, are actually two different and distinct compounds. The production of structurally different antimicrobial compounds by common species of Streptomyces is not an uncommon phenomenon, since there are abundant instances in the literature in which the same species of Streptomyces is known to produce more than one group of antibiotics (1,16).

BRIEF DESCRIPTION OF THE DRAWINGS

The invention is illustrated in the accompanying drawings, in which.

DETAILED DESCRIPTION OF THE PREFERRED EMBODIMENTS

In compliance with the constitutional purpose of the Patent Laws "to promote the progress of science and useful arts" (Article 1, Section 8), applicant submits the following disclosure of the invention.

MICROORGANISM

The organism was isolated from soil samples collected from fields in the vicinity of Lewiston, Idaho. *S. albovinaceous* can be maintained on potato dextrose agar, oatmeal agar (OMA), and glycerol-peptone-asparagine agar slants or plates or both. For long-time storage the organism was transferred to sterile soil and kept at room temperature. In sterile soil the organism remained viable for more than 6 months.

Isolation and Purification

Streptomyces strains (124 and 275) ATCC# 53453 and 53454 used to produce the novel antibiotic of the invention were isolated from soil samples collected from fields in the vicinity of Lewiston, Idaho. The soil samples were collected within 10–15 cm of depth from the soil surface. Such soil samples collected in several locations were mixed together and 10 g of soil was added to 90 ml of sterile water and were agitated on a shaker for 15 min. The sample was taken out of the shaker and allowed to settle for 15 min. The supernatant liquid was used for the isolation of Streptomyces. A serial dilution plate technique and a selective medium for the growth of Streptomyces were employed. After 4–5 days of growth at 30° C. the individual colonies were transferred to potato dextrose agar (PDA) medium.

Maintenance of Cultures

For short-time storage, the organisms were maintained in PDA or oatmeal agar (OMA), and glycerol-peptone-asparagine agar slants or plates or both. For long-time storage, the organisms were stored in sterile soil culture tubes. For this procedure the soil samples, which were collected in several locations, were mixed and then dispensed into 20 ml screw-capped tubes. The soil inside the tubes was moistened with water (to a little excess of field capacity) and were then sterilized under steam for 3 hours. After cooling, the sterile (still moist) soil was inoculated with the organism, which was then allowed to grow at room temperature for about 2–3 weeks. Such soil cultures can be stored at room temperature for several years without significant loss of viability or variability of the stored organism.

Taxonomic and Morphologic Characterization of the Organisms

Streptomyces sp. isolates 124 and 275 were characterized by the methods developed by collaborators of the International Streptomyces Project for the identification of Streptomyces species (1, 7, 8, 10-14). Identification was made by using Nonomura's classification key (7) and *Bergey's Manual of Determinative Bacteriology* (1). The color of mature aerial mycelia was observed on OMA, potato dextrose agar, and Pridham and Gottlieb's basal agar with glucose (8). The colony color on the reverse side of the plate was observed on potato dextrose agar, OMA, and tyrosine-casein-nitrate agar. Color standards and color nomenclature were used to describe the colony color. The production of melanoid pigments was examined on peptone-iron agar, tyrosine agar, and tryptone-yeast extract broth. Carbon utilization by the organism was studied on Pridham and Gottlieb's basal agar with various carbon sources added (8).

The morphologies of sporophores, spores, and spore surfaces were determined with a scanning electron microscope. For this study the organism was cultured on OMA for 1 week at 30° C. The material was fixed in 3% glutaraldehyde, stained in 2% osmium tetroxide solution, and dehydrated through a graded ethanol series. Material was then subjected to critical-point drying and sputter coated with gold.

Figure 1:
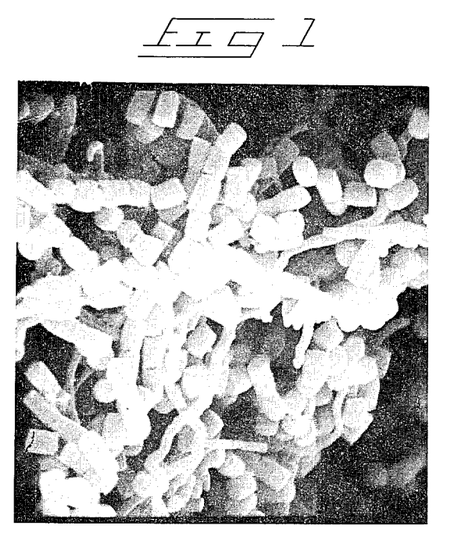
FIG. 1 is a scanning electron micrograph of *Streptomyces albovinaceous* strain 124.
Figure 2:
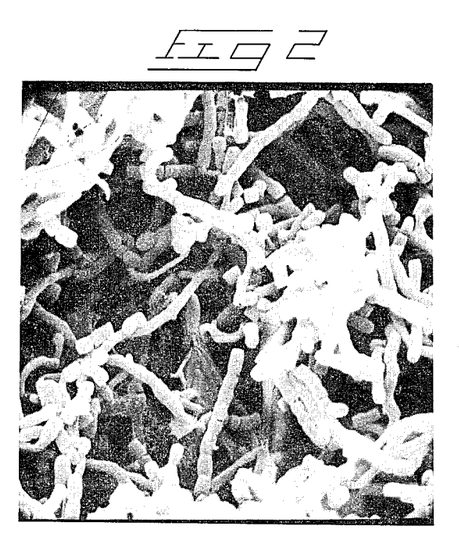
FIG. 2 is a scanning electron micrograph of *Streptomyces albovinaceous* strain 275.

Characteristics of the organism. The morphological and physiological characteristics of the organism are summarized in Table 1. By using the International Streptomyces Project classification scheme and *Bergey's Manual of Determinative Bacteriology* (1), the organism can be classified readily under Actinomycetales, family Streptomycetaceae, genus Streptomyces, and species albovinaceous. The organism utilized all carbon sources tested except inositol and raffinose (Table 1). In liquid culture it produced light wine red-colored pigment, but it was negative for melanin production. *S. albovinaceous* produced coenocytic aerial mycelia with abundant oidiospores on OMA, potato dextrose agar, and other microbiological media that are commonly used to grow actinomycetes. The spores were cylindrical (0.7 by 1.2 μm) and smooth walled (FIG. 1) and were formed on flexuous sporophores.

Colony Characteristics

Both strains of Streptomyces (124 and 275) can be grown readily on oatmeal agar (OMA), potato dextrose aga (PDA), glycerol-peptone-asparagine agar, corn meal agar and other commonly used microbiological media. The following specific characteristics of these strains were observed when they were grown on the following media.

OMA—Both the strains produced white aerial mycelia with a light yellowish appearance. On this medium no pigment was produced.

PDA—This is an excellent medium for the production of aerial mycelia and for spore production. The color of the aerial mass was white and the reverse side of the colony color was light grayish yellow.

Tyrosine Agar—Similar to PDA, the growth and sporulation of the organism were excellent. The aerial mass, especially that of 124, was pinkish white and a light pink colored pigment was also produced in the medium. No melenin was produced.

Peptone-Yeast-Extract Iron Agar—Very poor growth was observed. No melenin was produced.

Glucose-Peptone-Asparagine Agar (GPAA)—In all the other mentioned media except GPAA, the growth characteristics of the strains were indistinguishable. When grown on GPAA the strain 124 produced yellowish gray aerial mycelia with a yellow color underneath whereas the strain 275 on this medium produced white aerial mycelia with no yellow pigment underneath. Also, when grown in potato dextrose broth or oatmeal broth (in shakers or in fermentors) the strain 275 produced light pink pigment and 124 produced light yellow colored pigment.

TABLE 1

Morphological and physiological characteristics of Streptomyces sp. isolates 275 and 124

| Characteristics tested | Result |
| --- | --- |
| Aerial mass color | White |
| Melanoid pigment production | None |
| Reverse-side pigment | Not produced |
| Soluble pigment | Not produced |
| Spore chain morphology | Sporophores, flexuous (10 to 20 spores per sporophere) |
| Spore wall ornamentation or spore surface | Smooth-walled oidiospores (cylindrical, measuring 1.2 by 0.8 μm) |
| Carbon utilization" | |
| Arabinose | + |
| Xylose | + |
| Inositol | − |
| Mannitol | + |
| Fructose | + |
| Rhamnose | + |
| Sucrose | + |
| Raffinose | − |
| Starch | + |
| Glucose | + |
| Galactose | + |
| Salicin | + |
| Antibiotic production | Produces dienenitrile antibiotic |
| Streptomycin susceptibility | Inhibited at 50 μg/ml, but not at 10 μg/ml |
| Identification | *Streptomyces albovinaceous* |

"+,Carbon utilized; −,carbon not utilized.

Production of the antibiotic. Cultures of Streptomyces sp. isolates 124 and 275, which were grown on glucose-peptone agar (in grams per liter of distilled water: glucose, 10.0; peptone, 1.0; $MgSO_4.7H_2O$, 0.5; $K_2HPO_4$, 0.5; asparagine, 0.5; agar, 20.0), were used to inoculate 500-ml Erlenmeyer flasks containing 200 ml of sterile oatmeal broth at pH 6.5. Rolled osts were homogenized to a fine powder in a Waring blender before addition to the culture media. For preparation of the oatmeal broth a 20-g quantity of powdered oats was suspended in 1 liter of tap water and sterilized for 35 min. No additional carbon, nitrogen, or mineral sources were added. The seed culture was grown in this medium for 4 days at 28° C. on a reciprocating shaker set at 250 rpm. A fermentor jar containing 10 liters of the aforementioned sterile oatmeal broth was inoculated with the seed culture, allowed to grow aerobically for 6 days at 28° C. with 2 liters of sterile air per min, and agitated at 300 rpm.

Antimicrobial assays and mammalian toxicity. The antimicrobial activities of the fermentation broth, the crude solvent extract of the broth, and the purified antibiotic samples were tested by using the paper disk agar diffusion bioassay method against *Bacillus subtilis* and *Saccharomyces cerevisiae* as the test organisms.

The MICs of treponemycin on several species of bacteria and fungi were determined by the agar diffusion method. The MICs against four strains of *T. hyodysenteriae* were determined in vitro by incorporating the antibiotic into a blood agar similar to that described by Songer et al. (15). The strains of *T. hyodysenteriae* used for inoculation were cultivated in a liquid medium similar to that described by Kinyon and Harris (4). Bottled culture flasks inside GasPak jars (BBL Microbiology Systems) were shaken during incubation at 37° C. for 2 to 3 days. The number of cells used was standardized microscopically to approximately $10^6$, 0.1 ml of which was used for inoculation.

The 50% lethal dose of the antibiotic on mice was determined after oral administration of the antibiotic.

Isolation and purification. After 6 days of growth the whole broth was extracted twice, each time with 3 liters of methylene chloride. As an alternate procedure the active substance can be extracted with other water-immiscible organic solvents such as ethyl acetate, chloroform, butanol, and diethyl ether. Methylene chloride is the preferred solvent since it is less volatile, does not form troublesome emulsions, and also is nonpolar enough to leave behind some polar impurities. Both fractions of methylene chloride extracts were combined and concentrated under reduced pressure to a viscous yellow liquid. The crude material (2 to 3 g) was dissolved in chloroform (10 ml) and adsorbed on a dry Silica Gel G column (2.5 by 30 cm packed Silica Gel G60; particle size, 0.04 of 0.063 mm; E. Merck AG). The column was washed successively with 1 liter each of petroleum ether, methylene chloride, and chloroform, which removed most of the pigments and nonpolar impurities. The active material along with some impurities was eluted with a mixture of chloroform-acetone (9:1, vol/vol). After removal of the solvent, the active fraction was applied to silica gel preparative thin-layer chromatographic (TLC) plates (Baker Si 250F) and developed with an ethyl acetate-acetone mixture (2:1, vol/vol.). On the chromatogram under UV light, the active compound appeared as a dark quenching band that was scraped off the TLC plate and extracted with acetone. The antibiotic was crystallized from chloroform-hexane as light-yellow crystals (450 mg).

The homogeneity of the antibiotic was determined in different solvent systems, using TLC. On these chromatograms the antibiotic was visualized under UV light and also by the Libermann reagent (concentrated $H_2SO_4$-ethanol, 11:9). The homogeneity of the antibiotic was also checked by high-pressure liquid chromatography techniques with a reverse-phase $C_{18}$ column (Aquapore RP-300, 10 $\mu$m), using acetonitrile and trifluoroacetic acid-water (0.1% trifluoroacetic acid in water) as eluting solvents. The antibiotic was detected in the column effluents at 254 nm.

Spectroscopic procedures. UV and visible spectra of the antibiotic were measured in spectral-grade methanol on a Gilford 3600 spectrophotometer. Infrared (IR) spectra of the antibiotic and its chemical derivatives were taken in chloroform on a Beckman spectrophotometer, model Acculab 1. Proton magnetic resonance (PMR) and $^{13}C$-magnetic resonance spectra of the antibiotic and its derivatives were recorded on a Nicolet magnetic resonance spectrometer, model NT-20WB, at 200.042 MHz in deuterated chloroform, using tetramethylsilane as an internal reference. The mass spectrum of the antibiotic was taken with a Hewlett-Packard 598 gas chromatograph-mass spectrometer.

The specific rotation of the antibiotic was measured in chloroform solution at the 546-nm line of a mercury lamp with a Jasco-Dip-181 polarimeter.

Elemental analysis. Elemental analysis was performed in duplicate by Galbraith Laboratories.

Hydrogenation of the antibiotic. The antibiotic (70 mg) was dissolved in 5 ml of 95% ethanol in a 25-ml round-bottom flask to which a 10% palladium-on-charcoal catalyst (6 mg) was added. The hydrogenation was carried out at ambient temperature (20° C.) under 1 atm of hydrogen pressure for 90 min. At the end of 90 min the contents of the flasks were filtered and washed twice with 95% ethanol and dried under reduced pressure. The resultant residue was dissolved in 1 ml of chloroform, applied on a silica gel column, and eluted with a solvent mixture of chloroform-ethyl acetate (2:1). The hydrogenated product was crystallized from methylene chloride-hexane as a white crystalline product (60 mg).

In another experiment hydrogenation was carried out for 180 min. A 40-mg sample of the antibiotic was dissolved in 4 ml of absolute ethanol in a 25-ml round-bottom flask to which 3 mg of a 10% palladium-on-charcoal catalyst was added. Hydrogenation under 1 atm of pressure of hydrogen gas was carried out for 180 min. At the end of hydrogenation, the contents were filtered and the solvent was evaporated to dryness. The residue was crystallized in a methylene chloride-hexane mixture (36 mg).

Esterification of the antibiotic. A 50-mg sample of the antibiotic was dissolved in 5 ml of methanolic potassium hydroxide (1N), with stirring at room temperature for 16 h. The reaction mixture was diluted with water (60 ml), acidified with 2N HCl, and extracted twice with 50 ml of diethyl ether. The ether extract was treated with diazomethane, which was generated from alcoholic KOH and Diazatid (Aldrich Chemical Co.). At the end of the reaction the excess diazomethane was allowed to escape at room temperature or until the liquid was colorless. The solution was dried under vacuum, and the resulting material was found to be homogeneous by TLC.

The antibiotic compound: Treponemycin, can be utilized to produce its tetrahydro derivative, its primary amine, readily hydrolyzable esters, salts of these compounds and hydrates of these compounds and of the esters or salts. As readily hydrolyzable esters of the antibiotic compound there are to be understood compounds in which the carboxy group is present in the form of a readily hydrolyzable ester group. Examples of such esters, which can be of the conventional type, are the lower alkanoyloxyalkyl esters (e.g. the acetoxymethyl, pivaloyloxymethyl, 1-acetoxyethyl and 1-pivaloyloxyethyl ester), the lower alkoxycarbonyloxyalkyl esters (e.g. the methoxycarbonyloxymethyl, 1-ethoxycarbonyloxyethyl and 1-isopropoxycarbonyloxyethyl ester), the lactonyl esters (e.g. the phthalidyl and thiophthalidyl ester), the lower alkoxymethyl esters (e.g. the methoxymethyl ester) and the lower alkanoylaminomethyl esters (e.g. the acetamidomethyl ester). Other esters (e.g. the benzyl and cyanomethyl esters) can also be used.

A variety of pharmaceutically acceptable salts can be prepared from the free acid form of the antibiotic that is obtained through the esterification procedure outlined in the preceding paragraph. After the lactone or ester function in the molecule of the antibiotic is opened by acidification with hydrochloric acid, specific salts can be readily prepared by methods well known in the art; for example, by washing the free acid in solution with a suitable base or salt.

Examples of such pharmaceutically acceptable basic substances capable of forming salts for the purpose of the present invention include alkali metal bases, such as sodium hydroxide, potassium hydroxide, lithium hydroxide and the like; alkaline earth metal bases, such as calcium hydroxide, barium hydroxide and the like; and ammonium hydroxide. Alkali metal or alkaline earth metal salts suitable for forming pharmaceutically acceptable salts can include anions such as carbonates, bicarbonates and sulfates.

Examples of organic bases forming pharmaceutically acceptable salts are lower primary, secondary and tertiary alkyl amines, and hydroxy alkylamines such as ethylamine, isopropylamine, diethylamine, methyl-n-butylamine, ethanolamine and diethanolamine.

When by the above process a salt or an ester is obtained, this can be transformed into the free acid in a known manner and, vice versa, it will be evident that the free acid or a salt can be esterified by well-known methods.

Figure 4:
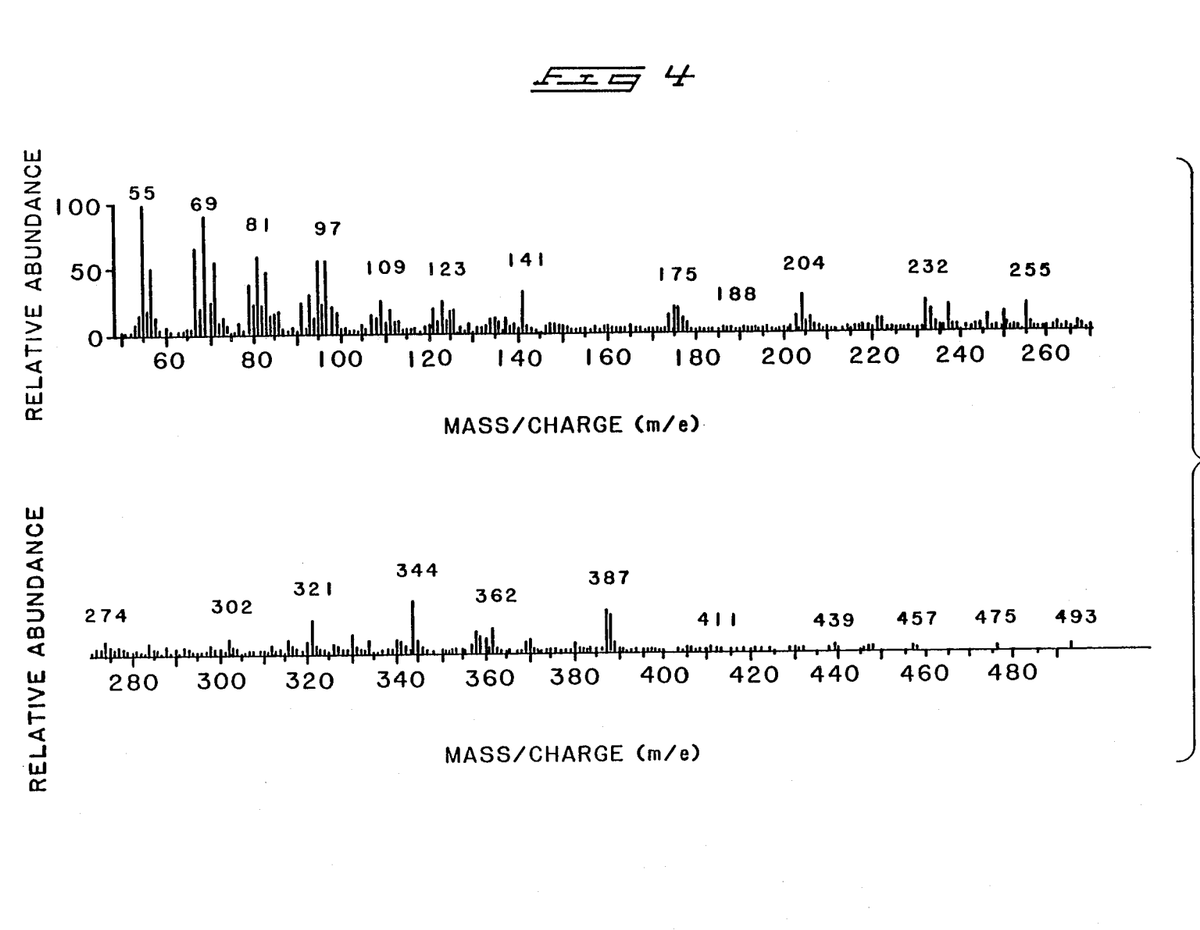
FIG. 4 is a mass fragmentation pattern for Tetrahydrotreponemycin.

Tetrahydro derivative of the antibiotic. A brief 90-min hydrogenation of the parent molecule resulted in the formation of a major white crystalline product. This was purified by TLC and later found to be homogenous by TLC plate assay (methylene chloride-methanol, 9:1, $R_f$ 0.58). The IR and PMR spectra of the product showed no characteristic absorptions for unsaturation; however, there was a peak at 2,220 cm$^{-1}$ in the IR spectrum. Moreover, an increase of four mass units in the molecular ion (M+493) as well as major fragments above m/e 383 suggested that the compound was the tetrahydro derivative of the parent antibiotic (FIG. 4). The antimicrobial activty of the tetrahydro derivative remained unchanged when compared with that of the parent antibiotic.

Figure 7:
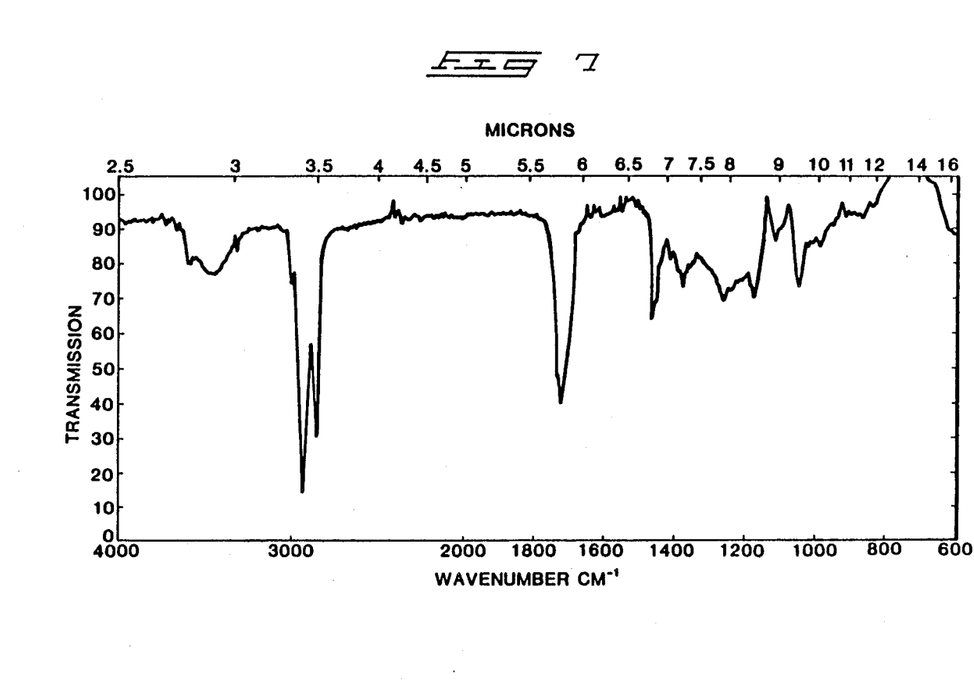
FIG. 7 is an infrared spectra of Treponemycin, amine in chloroform

Primary amine of the antibiotic. An extended 180-min hydrogenation of the antibiotic resulted in formation of another white crystalline compound with a specific rotation, $[_{546}]^{21}$, of −10.154 (C, 3.25; CHCl$_3$). The IR spectrum of this product revealed the absence of bands at 2,220 (nitrile stretching), 1,635 (C=C stretching), and 965 cm$^{-1}$ (substituted olefin) and the presence of two peaks in the region of 3,300 to 3,500 cm$^{-1}$ for a primary amine (N—H stretching) (FIG. 7).

Figure 6:
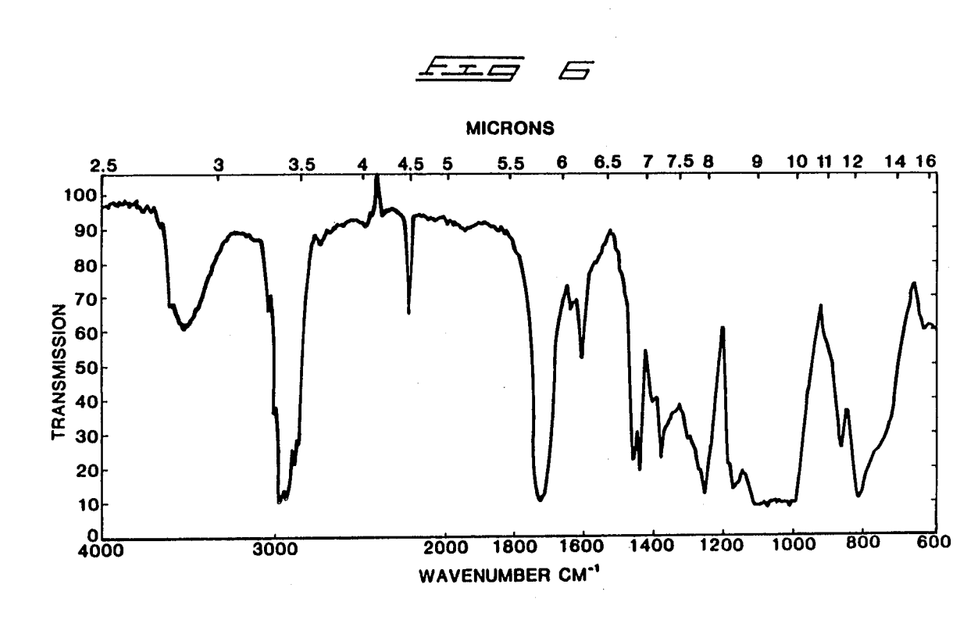
FIG. 6 is an infrared spectra of Treponemycin, dimethyl ester in chloroform.

Dimethyl ester of the antibiotic. Esterification of the antibiotic resulted in formation of a dimethyl ester. IR spectra (FIG. 6) showed bands at 3,520 (OH stretching) and 1,730 (lactone or ester carbonyl) cm$^{-1}$ and a sharp band at 1,260 cm$^{-1}$ (C—O stretching). Morover, the PMR spectrum of the product furnished a sharp singlet for six protons at δ3.74, indicating the presence of two methyl esters in the molecule and two singlets at δ3.32 (1H) and 3.3 (1H) for hydroxyl protons.

Treponemycin hydrochloride—20 mg of Treponemycin amine was dissolved in 10 ml of methanol. To that, 5 ml of 0.1N HCl was added. After mixing, the sample was lyophilized (freeze dried) to obtain Treponemycin hydrochloride.

Figure 3:
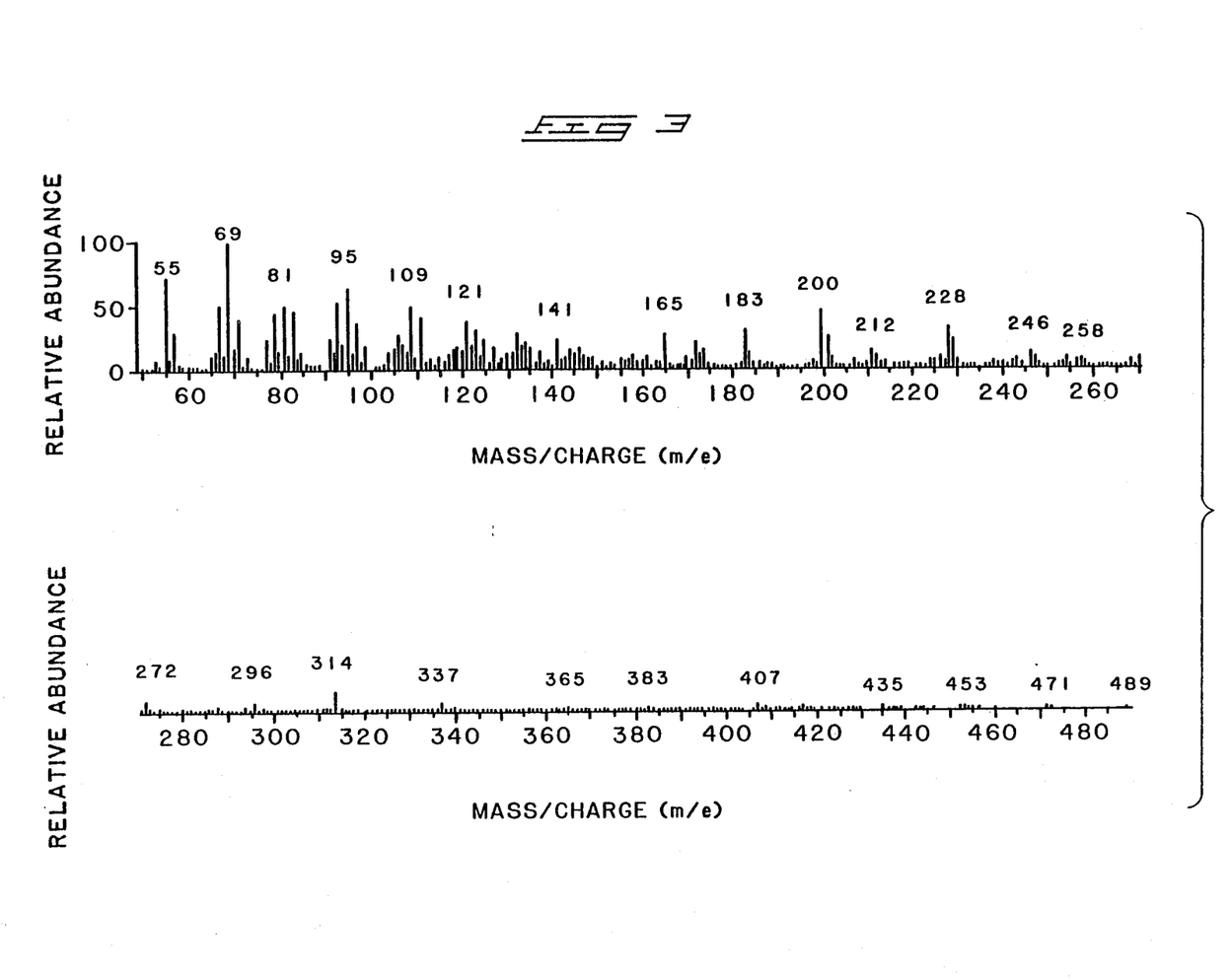
FIG. 3 is a mass fragmentation pattern for Treponemycin.
Figure 8:
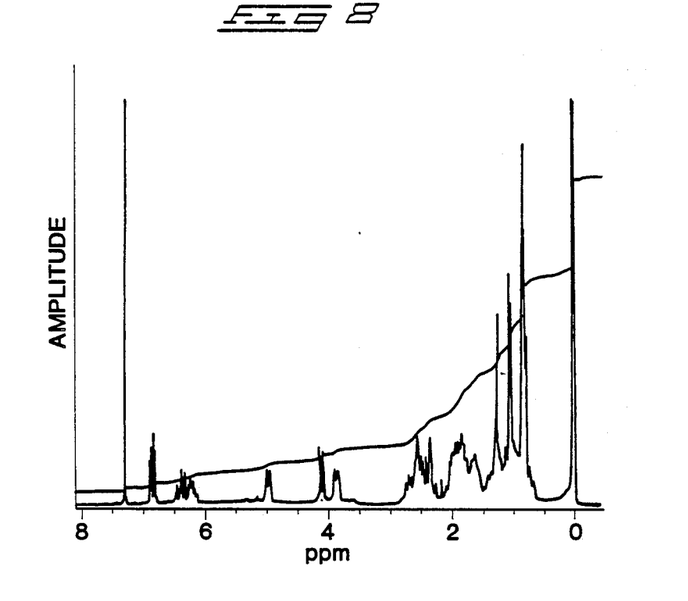
FIG. 8 is a proton magnetic resonance spectra of Treponemycin in deuterochloroform.
Figure 9:
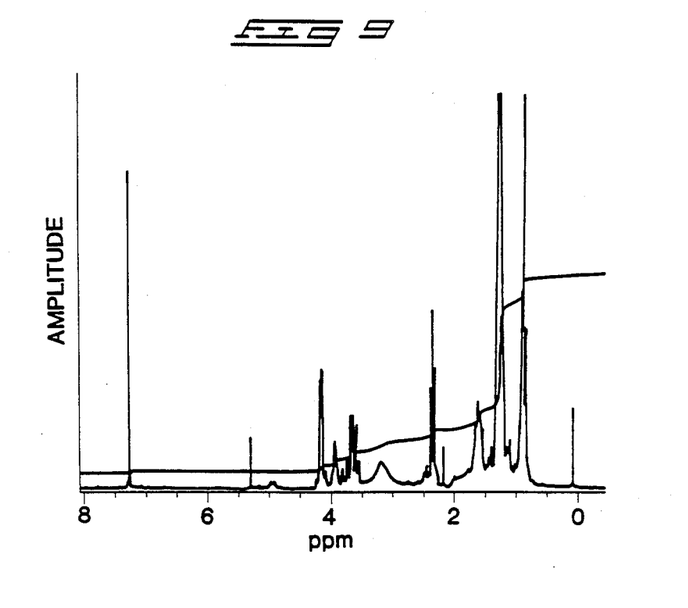
FIG. 9 is a proton magnetic resonance spectra of Treponemycin, amine in deuterochloroform.

Physical, chemical, and biological properties of the antibiotic. (i) The parent compound. The antibiotic as purified was homogeneous by both TLC and high-pressure liquid chromatography. Treponemycin is a light-yellow-colored substance with an mp of 93° to 93.5° C. and a specific rotation, $[\alpha]_{546}^{21}$, of −17.47 (C, 4.3; CHCl$_3$). It is soluble in most organic solvents, such as methylene chloride, acetone and chloroform, but is not soluble in ether, hexane, and carbon tetrachloride. The mass spectrum furnished a molecular ion peak at m/e 489 (FIG. 3), which is consistent with a molecular formula of C$_{28}$H$_{43}$O$_6$N (found: C$_{68.82}$, H$_{9.13}$, N$_{2.84}$, O$_{19.21}$ by difference; calculated: C$_{69.32}$, H$_{8.76}$, O$_{19.12}$, N$_{2.79}$). The IR spectrum (FIG. 5) of the antibiotic in chloroform showed absorptions at 3,000 (olefinic C—H stretching), 2,950, 2,910, 2,220 (nitrile stretching), 1,720 (lactone or ester), 1,700 (carbonyl stretching), 1,635 (C=C stretching), 1,460, 1,375, 1,250, 1,170, 1,025, and 965 cm$^{-1}$ (substituted olefinic). The presence of an olefinic group and a sharp band for a nitrile function at 2,220 cm$^{-1}$ suggested that the nitrile group may be attached to an unsaturated carbon. Furthermore, the UV spectrum of the compound in methanol gave UV maxima at 257 nm, which confirms the presence of a conjugated dienenitrile group in the molecule:

The PMR spectrum (FIG. 8) of the antibiotic in deuterochloroform, using tetramethylsilane as internal standard, indicated the presence of 43 protons, 3 of which were attached to the conjugated olefinic system. A downfield doublet at δ6.81 (1H, J=11 cps) was assigned to the proton adjacent to the nitrile function. There were two multiplets at 6.40 (1H). The downfield doublet at δ4.97 (1H, J=11 cps) suggested that the lactone or ester function of the antibiotic terminates on a secondary carbon atom Four quarternary methyl groups absorb at δ0.79, 0.82, 0.85, and 1.25. The downfield singlet at δ1.25 suggests that three protons are attached very near to he carbonyl ester or olefinic function. The doublet for six protons at δ1.043 (J=6 cps) suggests the presence of a system in the molecule. The spectrum did not show the presence of any carboxylic acid proton or hydroxyl proton since none of the protons was exchanged with D$_2$O.

The $^{13}$C-magnetic resonance of the antibiotic showed absorption lines at δ207.74, 177.65, and 172.25. This suggested that the antibiotic must have at least one carbonyl and two lactone or ester groups, which altogether accounted for five oxygen atoms. Since there was no D$_2$O-exchangable proton in the PMR spectrum and no absorption band for hydroxyl groups in the IR spectrum, we deduced that the remaining oxygen atom in the molecule might be present as an ether (—C—O—C—) linkage. This inference was confirmed from the $^{13}$C-magnetic resonance spectrum of the antibiotic, which had four absorption lines, two for lactone or ester and two for ether, in the region of δ80–70, which is the characteristic absorption range for carbons bonded singly with oxygen. The pesence of four olefinic and one nitrile carbon was also confirmed from the $^{13}$C-magnetic resonance spectrum, which exhibited five absorption lines in the region δ119.0 to 144.0.

Assignment of nitrile, diene, and other functional groupings in the molecule of treponemycin is based on spectroscopic and chemical analyses of the antibiotic and its derivatives. A sharp absorption band at 2,200 cm$^{-1}$ in the IR spectrum followed by an absorption line at 144.00 in the $^{13}$C-magnetic resonance spectrum indicate the presence of a nitrile group in the molecule.

Furthermore, the suggested molecular formula of $C_{28}H_{43}O_6N$ and a yield of 1 mol of ammonia per mole of the compound upon acid hydrolysis not only indicate the presence of a nitrile group but also confirm the presence of only one nitrile group in the molecule.

Although a nitrile or isonitrile functional group is rarely found in natural products (2, 6), recently a group of isonitrile-containing compounds was isolated from several species of the soil-inhabiting fungus Trichoderma (3). In addition, an inhibitor (A32390A) of dopamine $\beta$-hydroxylase, which is also an antimicrobial compound, was isolated and characterized (5). The chemical, physical, and biological properties of these compounds appear to be different from those of treponemycin (2, 3, 5, 6).

Assignment of a diene function in the molecule was also made on the basis of PMR and $^{13}$C-magnetic resonance spectra of treponemycin; the spectra further indicate that the molecule may contain three olefinic protons and four unsaturated carbons in addition to nitrile carbon. The UV spectrum of the compound in methanol furnished an absorption maximum at 257 nm, which is a strong indication of a nitrile group, possibly conjugated with a diene system, since saturated nitriles are transparent in the near-UV region (9) and the $\alpha,\beta$-unsaturated nitriles absorb at 257 nm. Hence all of these observations strongly suggest that the three olefinic protons of the diene system are in conjugation with that of a nitrile group. In addition, a doublet at $\delta 6.81$ for one proton (J=11 cps) was assigned for the hydrogen attached to $\alpha$-carbon with respect to nitrile, which is trans to the hydrogen ($\delta 6.40$) at $\beta$-carbon. The remaining olefinic proton appeared at $\delta 4.97$ (1H, J=11 cps) and suggested that the lactone or ester function in the molecule terminates on a secondary carbon Absence of any D$_2$O-exchangable protons in the molecule clearly excludes the presence of hydroxyl or carboxyl groupings in the molecule. In addition, there is not evidence of loss of 44 mass units for CO$_2$ from molecular ion or fragment ions of high mass of the parent compound or its tetrahydro derivative; this substantiates the absence of a carboxylic group in the molecule.

Figure 5:
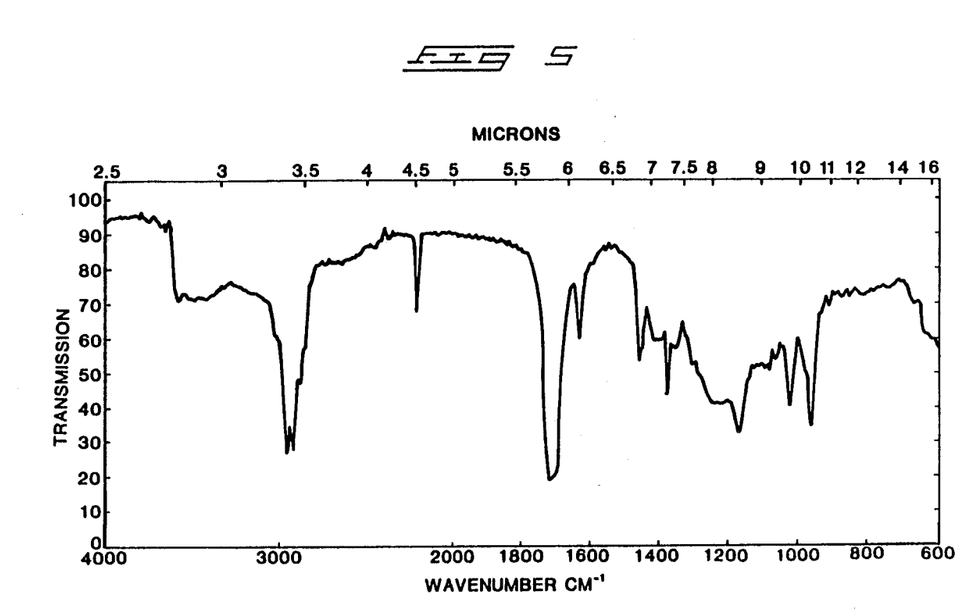
FIG. 5 is an infrared spectra of Treponemycin in chloroform.

The assignment of carboxyl, lactone, or ester and ether groupings in the molecule was based on IR and $^{13}$C-magnetic resonance spectra of the antibiotic. Absorption lines were assigned at $\delta 207.74$ for carboxyl and at $\delta 177.65$ and $172.25$ for lactone or ester; of four absorption lines in the region of $\delta 80-70$ of the $^{13}$C-magnetic resonance spectra, two were assigned for lactone or ester and two were assigned for ether. These observations were further suppored by the IR spectrum (FIG. 5).

Brief hydrogenation of the molecule resulted in complete reduction of the diene part of the molecule, but the nitrile function of the compound remained intact, as shown by the presence of IR absorption bands at 2,220 cm$^{-1}$. Bioassay of this product showed no loss in antimicrobial activity when compared with the parent compound. The longer hydrogenation of the antibiotic yielded a primary amine which showed no antimicrobial activity. In addition, hydrolysis and esterification of the antibiotic resulted in formation of a dimethyl ester which again showed no antimicrobial activity. In the dimethyl ester of the antibiotic molecule, opening of the lactone ring possibly resulted in total loss of biological activity, even though the diene and nitrile functions were intact. This suggests that the stereospecificity of the molecule is essential for the antimicrobial property. It also suggests that both nitrile and lactone functions are needed for this molecule to exhibit antimicrobial activity.

TABLE 2

| Antibiotic spectrum of treponemycin | |  |
|---|---|---|
| Microorganism | MIC ($\mu$g/ml) | |
| Actinomyces viscosis | <0.5 | |
| Bacillus subtilis | 1.0 | |
| Bacteriodes fragilis | 5.0 | |
| B. multiacidus | >100.0 | |
| Clostridium perfringens | >100.0 | |
| C. septicum | >100.0 | |
| Erwinia amylovora | 50.0 | |
| Escherichia coli | >100.0 | |
| Fusobacterium necrophorum | <0.1 | |
| Lactobacillus acidophilus | 50.0 | |
| Pseudomonas aeruginosa | >100.0 | |
| Salmonella typhimurium | >100.0 | |
| Sarcina lutea | <0.1 | |
| Staphylococcus aureus | 100.0 | |
| Streptococcus faecalis | 25.0 | |
| S. mutans | 50.0 | |
| S. bovis | >100.0 | |
| Treponema hyodysenteriae strain | >2.5 | <5.0 |
| B-78 | >2.5 | <5.0 |
| B-140 | >2.5 | <5.0 |
| B-169 | >2.5 | <5.0 |
| T-9-J | >2.5 | <5.0 |

Uses of the Antibiotic

The MIC's of Treponemycin for selected bacteria are presented in Table 2. The antibiotic is active against mainly gram-positive and a few gram-negative species of bacteria, bacteriodes, and actinomyces. When tested, treponemycin showed no activity against Candida albicans and Aspergillus niger. However, the antibiotic exhibited strong activity in vitro against the organisms associated with swine dysentery. Four strains of T. hyodysenteriae (Table 2) which were previously isolated from characteristic cases of swine dysentery and were also known to produce typical pathological symptoms in the mouse model (J. W. Whalen et al., presented at the Michigan Branch-Western Ontario Branch joint meeting, American Society for Cirobiology, 1982) were inhibited at or below 5 $\mu$g of the antibiotic per ml of test medium.

The 50% lethal dose (mouse) of the antibiotic was slightly less than 400 mg/kg of body weight.

As shown in Table 2. The novel antibiotic of the invention is highly effective in inhibiting several species of bacteria, especially Fusobacterium necrophorum and Treponema hyodysenteriae. Several species of bacteria belonging to the genus Fusobacterium are pathogenic to man and domestic animals, and usually occur in various prulent or gangrenous infections and in organ infarcts. Fusobacterium necrophorum often occurs in necrotic lesions, liver abscesses and in blood of man. It is also associated with the foot rot of cattle. Like the other species of Fusobacterium this organism exhibits high levels of resistance to erythromycin and other antibiotics. Since the antibiotic compound Treponemycin showed good activity against Fusobacterium necrophorum, it can be used for the control and treatment of infections caused by this and other related species of Fusobacterium, such as F. nucleatum, F. gonidiafor-

*mans, F. varium* and *F. necrogenes*. All these bacteria are opportunistic pathogens which are invariably present in abscesses, necrotic lesions, upper respiratory infections, surgical wounds, and prulent infections of man and domestic animals.

The antibiotic also showed good activity in vitro against four pathogenic strains of *Treponema hyodysenteriae*, the causal agents of swine dysentery, a disease of considerable economic importance in the swine industry. In view of its low mammalian toxicity (50% lethal dose of slightly less than 400 mg/Kg) and its strong activity against *T. hyodysenteriae* the antibiotic has a value as a swine dysentery therapeutic.

Since Treponemycin showed strong activity against all the strains of one species of Treponema, this compound will control and treat diseases caused by other following species of Treponema:

a. *T. pallidum* subspecies pallidum causes venereal and congenital syphilis in man, and is also pathogenic to monkeys.
b. *T. pallidum* subspecies pertenue causes yaws in man, a contagious disease that is spread by contact.
c. *T. pallidum* subspecies endemicum causes a contagious nonvenereal syphilis in man is endemic in Africa, the Middle East, Southest Asia and in Yugoslavia.
d. *T. carateium* causes pinta or carate, a contagious disease in man found in Mexico, Central America and parts of South America.

The novel antibiotic may be useful in the control and treatment of diseases caused by the other members of Spirochaetales. The genus Treponema is one of the three closely related genera of Spirochaetales, the members of which cause various diseases in man and animals. The members of the genus Borrelia are pathogenic to man, other mammals and birds which cause tick-borne and louse-borne relapsing fever in man (*Borrellia anserina, Borrellia reccurrentis* and eight other species of Borrellia). Leptospirai, another genus of Spirochaetales the members of which cause leptospirosis, is a zoonosis primarily infecting wild and domestic animals. *Leptospira interrogans* causes influenza-like illness in man.

Similar biologically useful results can be achieved by administration of the identified derivatives of the antibiotic, as well as salts of these compounds and hydrates of these compounds or salts.

The product of this invention may be administered alone, but will generally be administered with pharmaceutically acceptable, non-toxic carriers or emulsifiers, the proportions of which are determined by the suitability and chemical nature of the carrier, the chosen route of administration, and standard pharmaceutical practice. For example, in combatting various infections or in maintaining therapeutically effective levels in the blood or tissues, they may be administered orally in the form of tablets or capsules containing such excipients as starch, milk, sugar, certain type of clay, etc. They may be enteric coated so as to be more resistant of the acid and digestive enzymes of the stomach. For parenteral administration they may be used in the form of a sterile solution containing other solutes, for example, enough saline or glucose to make the solution isotonic. A wide variety of dosage unit forms are possible.

In the pharmaceutical compositions, the compounds of the invention can be used together with other suitable therapeutically active components, preferably with other antibacterially active compounds, such as beta-lactam antibiotics, e.g. penicillins or other aminopenicillanic acid derivatives, and cephalosporins. Also other antibacterially active substances are of interest in this connection, e.g. aminoglycosides. In combinations with beta-lactam antibiotics such as penicillins like ampicillin, amoxicillin, or carbenicillin, or cephalosporins like caphalothin, cefazolin or cephalexin, a synergistic effect is observed which is of importance in many clinical situations. Also a depression of development of resistance can be obtained by a combination therapy. In such compositions, the weight ratio between the active components appropriately is between 1:20 and 20:1, preferably within the ratios 1:5 and 5:1. These active components may be administered together or the compounds of this invention may be administered before or after the administration of another beta-lactam antibiotic.

The physician or veterinarian in attendance will determine the dosage regimen which will be effective. This will depend upon such factors as the age and weight of the patient, the degree and locus of the infection and the dosage unit form selected. Dosage unit forms containing from 25 to 250 mg are useful.

The following non-limiting examples are given by way of illustration only.

EXAMPLE I

Preparation of Tablets 1000 g of antimicrobial agent and 3000 g of lactose are thoroughly mixed together and the whole are passed through a 30 mesh sieve.

A paste is separately prepared with 80 g of corn starch and 350 ml of distilled water.

The above mixture is well kneaded with the paste and the mass is passed through a 4 mesh sieve. The resulting globules are dried at 30° C. for 15 to 20 hours.

The dried globules are then granulated first on a granulating machine and passed through a 16 mesh sieve. The grains are covered with a powdery mixture prepared by blending 30 g of calcium stearate, 200 g of corn starch and 80 g talc, and passed through a 40 mesh sieve.

Tablets, each containing 50 mg of antimicrobial agent are made of the above-obtained granules in accordance with the conventional procedure known in the art.

EXAMPLE II

Preparation of the antibiotic for intravenous, intraplural and/or for intra-peritonial injections.

A known quantity of antibiotic may be mixed with a suitable emulsifier such as Cremophor EL (from Sigma) before being used for injections.

A 100 g of antibiotic is taken in a quantity of distilled water and made up to 5 liters. The mixture is made isotonic with the addition of a predetermined amount of an aqueous solution of physiological salt. The solution is filtered, sterilized and aseptically dispensed into 5 ml pre-sterilized ampoules and sealed.

EXAMPLE III

For treatment and control of swine dysentery

Treponemycin in a ratio of 5 to 500 g/ton is mixed with a ton of complete feed as the sole ration for three weeks or until signs of disease (water mucoid or bloody stools) disappear. At a rate of 50 g of antibiotic per ton of feed is used in animals or on premises with a history of swine dysentery but where symptoms have not yet occurred. In several cases a known quantity of antibiotic is mixed with soybean meal feed as a carrier or diluent. The antibiotic can also be mixed with other carriers such as rice hulls, calcium carbonate, or sodium carboxymethyl cellulose.

A typical feed mix with antibiotic (150 g/ton) for swine dysentery control consists of the following ingredients (by weight):
(1) cereal grain (corn, wheat, barley, oats, triticale) 76% to 80%
(2) protein supplement (soybean meal, corn glutein meal, meat and bone meal, cotton seed meal, etc.) 14.5% to 20%
(3) vitamin premix, 0.5%
(4) trace minerals (premixed materials) 0.1%
(5) dicalcium phosphate 1.3%
(6) animal fat 1.0%

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

LITERATURE CITED

1. Buchanan, R. E., and N. E. Gibbons (ed.). 1974. Bergey's manual of determinative bacteriology, 8th ed. The Williams & Wilkins Co., Baltimore.
2. Evans, J. R., E. J. Napier, and P. Yates. 1976. Isolation of a new antibiotic from a species of Pseudomonas. J. Antibiot.
3. Fujiwara, A., T. S. Masuda, Y. Shioni, C. Miyamoto, Y. Sekine, M. Tazoe, and M. Fujiwara. 1982. Fermentation, isolation and characterization of isonitrile antibiotics. Agric. Biol. Chem. 46: 1803–1809.
4. Kinyon, J. M., and D. L. Harris. 1974. Growth of *Treponema hyodysenteriae* in liquid medium. Vet. Rec. 95: 219–220.
5. Marconi, G. G., B. B. Molloy, R. Nagarajan, J. W. Martin, J. B. Deeter, and J. L. Occolowitz. 1978. A32390A, a new biologically active metabolite. II. Isolation and structure. J. Antibiot. 31: 27–32.
6. Nobuhara, M., H. Tazima, K. Shudo, A. Itai, T. Okamoto, and Y. Itaka. 1976. A fungal metabolite, novel isocyano epoxide. Chem. Pharm. Bull. 24: 832–834.
7. Nonomura, H. 1974. Key for classification and identification of 458 species of the streptomycetes included in ISP. J. Ferment. Technol. 52: 78–92.
8. Pridham, T. G., and D. Gottlieb. 1948. The utilization of carbon compounds by some actinomycetes as an aid for species determination. J. Bacteriol. 56: 107–114.
9. Scott, A. I. 1964. Interpretation of the ultraviolet spectra of natural products, p. 39. The MacMillan Co., New York.
10. Shirling, E. B., and D. Gottlieb. 1966. Methods for characterization of Streptomyces species. Int. J. Syst. Bacteriol. 16: 313–340.
11. Shirling, E. B., and D. Gottlieb. 1968. Cooperative description of type cultures of Streptomyces. II. Species descriptions from first study. Int. J. Syst. Bacteriol. 18: 69–189.
12. Shirling, E. B., and D. Gottlieb. 1968. Cooperative description of type cultures of Streptomyces. III. Additional species descriptions from first and second studies. Int. J. Syst. Bacteriol. 18: 279–392.
13. Shirling, E. B., and D. Gottlieb. 1969. Cooperative description of type cultures of Streptomyces. IV. Species descriptions from the second, third, and fourth studies. Int. J. Syst. Bacteriol. 19: 391–512.
14. Shirling, E. B., and D. Gottlieb. 1972. Cooperative description of type strains of Streptomyces. V. Additional descriptions. Int. J. Syst. Bacteriol. 22: 265–394.
15. Songer, J. G., J. M. Kinyon, and D. L. Harris. 1976. Selective medium for isolation of *Treponema hyodysenteriae*. J. Clin. Microbiol. 4: 57–60.
16. Umezawa, H. (ed.). 1967. Index of antibiotics from Streptomyces, p. 2–81. University of Tokyo Press, Tokyo.

We claim:

1. An antibiotic compound Treponemycin which is a light-yellow crystalline substance in pure form having the following characteristics:
   a. a molecular formula of $C_{28}H_{23}O_6N$;
   b. a melting point of 93°–93.5° C.;
   c. includes a conjugated diene group of the formula d. an ultraviolet maxima at 257 nm;
   e. An infrared absorption spectrum in chloroform with absorption bands at 3000, 2950, 2910, 2220, 1720, 1700, 1635, 1460, 1375, 1250, 1170, 1025 and 965 cm$^{-1}$;
   f. an absence of any free hydroxyl or free carboxyl group; and
   g. is soluble in methylene chloride, acetone and chloroform but not soluble in petroleum ether, hexane and carbontetrachloride, or pharmaceutically acceptable salts thereof.

2. Treponemycin as defined in claim 1.

3. An alkali metal salt of Treponemycin, as defined in claim 1.

4. The hydrochloride of Treponemycin, as defined in claim 1.

5. A process for producing the antibiotic treponemycin as defined in claim 1, which comprises culturing at least one of strain 124 and 275 of *Streptomyces albovinaceous* (ATCC 53453 and 53454, respectively) in an aqueous nutrient medium, under aerobic conditions, until a recoverable quantity of Treponemycin is produced and recovering said Treponemycin from said medium.

6. A process according to claim 5, wherein said medium contains assimilable sources of carbon, nitrogen and inorganic salts.

7. An animal feed composition comprising an animal feed mixed with the antibiotic: Treponemycin as defined in claim 1, or pharmaceutically acceptable salts thereof.

8. An animal feed composition according to claim 7, wherein said animal feed contains said Treponemycin, or salts thereof in the ratio of 5 to 500 grams of antibiotic per ton of feed.

9. A pharmaceutical composition comprising:
   an effective amount of the antibiotic: Treponemycin as defined in claim 1 or pharmaceutically acceptable salts thereof; and a pharmaceutically acceptable carrier.

10. A method of combatting infectious bacterial diseases to a host in need thereof which comprises administering an antibacterial effective amount of the antibiotic: Treponemycin as defined in claim 1, or pharmaceutically acceptable salts thereof to said host.

11. A method of combatting dysentery in swine caused by *Treponema hyodysenteriae* which comprises administering to the affected animal an antibacterial effective amount of the antibiotic: Treponemycin as defined in claim 1 or a pharmaceutically acceptable salt thereof.

12. A method of combatting dysentery in swine caused by *Treponema hyodysenteriae* which comprises feeding the affected animal with a diet containing an antibacterial effective amount of the antibiotic: Treponemycin as defined in claim 1 or a pharmaceutically acceptable salt thereof.

13. A method of combatting dysentery in swine caused by *Treponema hyodysenteriae* which comprises feeding the affected animal with an antibacterial effective amount of a diet composed of the antibiotic: Treponemycin as defined in claim 1, or a pharmaceutically acceptable salt thereof, mixed with a complete feed in the ratio of 5 to 500 grams of antibiotic per ton of feed.

14. A method of combatting infectious bacterial diseases to a mammal which comprises administering an antibacterial effective amount of the antibiotic Treponemycin as defined in claim 1, or a pharmaceutically acceptable salt thereof to said mammal.

* * * * *